United States Patent
Nabika

(10) Patent No.: US 7,323,611 B2
(45) Date of Patent: Jan. 29, 2008

(54) PROCESS FOR PRODUCING OLEFIN OLIGOMER

(75) Inventor: Masaaki Nabika, Ichihara (JP)

(73) Assignee: Sumitomo Chemical Company Limited, Tokyo (JP)

( * ) Notice: Subject to any disclaimer, the term of this patent is extended or adjusted under 35 U.S.C. 154(b) by 44 days.

(21) Appl. No.: 11/423,009

(22) Filed: Jun. 8, 2006

(65) Prior Publication Data

US 2006/0293546 A1 Dec. 28, 2006

(30) Foreign Application Priority Data

Jun. 28, 2005 (JP) ............................. 2005-187836

(51) Int. Cl.
*C07C 2/24* (2006.01)
(52) U.S. Cl. ...................... 585/513; 585/512; 585/522; 585/523
(58) Field of Classification Search ................ 585/512, 585/513, 522, 523
See application file for complete search history.

(56) References Cited

U.S. PATENT DOCUMENTS 5,811,618 A * 9/1998 Wu ............................. 585/513
5,910,619 A * 6/1999 Urata et al. .................. 585/513
6,521,806 B1 * 2/2003 Tamura et al. ............... 585/512

FOREIGN PATENT DOCUMENTS

| WO | WO02/04119 A1 | 1/2002 |
|---|---|---|
| WO | WO03/053890 A1 | 7/2003 |
| WO | WO2004/056477 A1 | 7/2004 |
| WO | WO2004/056479 A1 | 7/2004 |

* cited by examiner

*Primary Examiner*—Fred Teskin
(74) *Attorney, Agent, or Firm*—Akin Gump Strauss Hauer & Feld LLP

(57) ABSTRACT

A process for producing an olefin oligomer, which comprises the steps of (1) contacting an olefin with an organoaluminum compound to produce a contact product (i), (2) contacting a transition metal compound with a compound represented by the formula, $R^1R^2A$-G-$AR^3R^4$, to produce a contact product (ii), and (3) contacting the contact product (i), the contact product (ii), an alumoxane compound, and optionally an olefin with one another, wherein A is a nitrogen atom, a phosphorus atom, an arsenic atom or an antimony atom, and As are the same as or different from each other; G is a divalent group; and $R^1$, $R^2$, $R^3$ and $R^4$ are independently of one another a hydrocarbyl group, a halogenated hydrocarbyl group, an oxygen-containing hydrocarbyl group, a sulfur-containing hydrocarbyl group, a selenium-containing hydrocarbyl group, or a tellurium-containing hydrocarbyl group.

10 Claims, No Drawings

PROCESS FOR PRODUCING OLEFIN OLIGOMER

FIELD OF THE INVENTION

The present invention relates to a process for producing an olefin oligomer with high productivity.

BACKGROUND OF THE INVENTION

WO 02/04119A1 discloses a process for trimerization of olefins comprising contacting a monomeric olefin or a mixture of olefins under trimerization conditions with a catalyst, which comprises (a) a source of chromium, molybdenum or tungsten, (b) a ligand containing at least one phosphorus, arsenic or antimony atom bound to at least one hydrocarbyl or heterohydrocarbyl group having a polar substituent, but excluding the case where all such polar substituents are phosphane, arsane or stibane groups, and optionally (c) an activator.

Also, WO 2004/056477A1 discloses a process for trimerisation of olefins, which process includes the steps of contacting an olefinic feedstream with a catalyst system which includes a transition metal compound and a heteroatomic ligand and wherein the trimer is an olefin and wherein the heteroatomic ligand is described by the following general formula $(R)_n A\text{-}B\text{-}C(R)_m$.

SUMMARY OF THE INVENTION

However, there is a problem in that said processes do not produce an olefin trimer with high productivity.

In view of the above-mentioned problem in the conventional art, the present invention has an object to provide a process for producing an olefin oligomer with high productivity.

The present invention is a process for producing an olefin oligomer, which comprises the steps of:
 (1) contacting an olefin with an organoaluminum compound, thereby producing a contact product (i);
 (2) contacting a transition metal compound with a compound represented by the following formula (1), thereby producing a contact product (ii); and
 (3) contacting the contact product (i), the contact product (ii), an alumoxane compound, and optionally an olefin with one another;

$$R^1R^2A\text{-}G\text{-}AR^3R^4 \qquad (1)$$

wherein A is a nitrogen atom, a phosphorus atom, an arsenic atom or an antimony atom, and As are the same as or different from each other; G is a divalent group; and $R^1$, $R^2$, $R^3$ and $R^4$ are independently of one another a hydrocarbyl group, a halogenated hydrocarbyl group, an oxygen-containing hydrocarbyl group, a sulfur-containing hydrocarbyl group, a selenium-containing hydrocarbyl group, or a tellurium-containing hydrocarbyl group.

DETAILED DESCRIPTION OF THE INVENTION

The olefin in the present invention means an unsaturated hydrocarbon containing one or more carbon-carbon double bonds. Examples of the olefin are ethylene, propylene and 1-butene. Among them, ethylene is preferable from a viewpoint of industrial availability.

The organoaluminum compound in the present invention means a compound containing a direct bond between a carbon atom and an aluminum atom. Examples of the organoaluminum compound are trimethylaluminum, triethylaluminum, tri-n-butylaluminum, triisobutylaluminum, tri-tert-butylaluminum, tri-n-hexylaluminum, tri-cyclohexylaluminum, tri-n-octylaluminum, dimethylaluminum chloride, dimethylaluminum bromide, diethylaluminum chloride, diethylaluminum bromide, diisobutylaluminum chloride, diisobutylaluminum bromide, and an alumoxane compound. Among them, preferred is trimethylaluminum, triisobutylaluminum, tri-n-octylaluminum or an alumoxane compound, from a viewpoint of industrial availability. Examples of the alumoxane compound are those of another alumoxane compound used in the step (3) mentioned hereinafter.

An example of a method for contacting the olefin with the organoaluminum compound in the step (1) is a method comprising the sub-steps of (1-1) feeding separately the olefin and a solution containing the organoaluminum compound to a reactor, and (1-2) contacting them in the reactor, thereby producing the contact mixture. Said contact mixture may be directly used in the step (3) as the contact product (i). The step (1) is carried out usually at a temperature of 0 to 200° C. and usually under a pressure of 0.01 to 10 MPa. A contact time in the step (1) is usually 1 minute to 24 hours, and preferably 1 minute to 1 hour. The contact time of shorter than 1 minute may result in insufficient productivity of an olefin oligomer.

The organoaluminum compound in the step (1) is used in an amount of preferably 1 to 1,000 parts by mol per 1 part by mol of the transition metal compound used in the step (2). Said amount of smaller than 1 part by mol may result in insufficient productivity of an olefin oligomer, and said amount of larger than 1,000 parts by mol may result in low selectivity of an intended olefin oligomer.

While a ratio of an amount of the organoaluminum compound used in the step (1) to an amount of the olefin used therein depends upon an amount of an impurity such as a polymerization inhibitor (for example, water and oxygen) contained in said olefin, the organoaluminum compound in the step (1) is used in an amount of preferably 0.00001 to 0.01 part by mol per one part by mol of the olefin used the step (1). Said amount of smaller than 0.00001 part by mol may result in insufficient productivity of an olefin oligomer, and said amount of larger than 0.01 part by mol may result in low selectivity of an intended olefin oligomer.

The transition metal compound in the present invention means a compound containing an element belonging to Groups 3 to 11 of the periodic table. The transition metal compound is preferably a chromium compound, a molybdenum compound, or a tungsten compound. Among them, more preferred is a chromium compound from a viewpoint of higher productivity of an olefin oligomer.

Examples of the chromium compound are those represented by the following formula (2):

$$CrJ_jM_m \qquad (2)$$

wherein J is an oxygen atom, a halogen atom, a monovalent hydrocarbyl group, an oxygen atom-containing monovalent hydrocarbyl group, or a two substituent-carrying monovalent amino group, and when plural Js exist, they are the same as, or different from one another; j is an integer of 0 to 5; M is a group bound to the chromium atom with a lone electron-pair or π electrons, and when plural Ms exist, they are the same as, or different from one another; m is an integer of 0 to 6; and j and m satisfy $2 \leq j+m \leq 6$.

Examples of the halogen atom of J in the formula (2) are a fluorine atom, a chlorine atom, a bromine atom, and an iodine atom.

Examples of the monovalent hydrocarbyl group of J in the formula (2) are a methyl group, an ethyl group, a n-propyl group, an isopropyl group, a n-butyl group, a sec-butyl group, a tert-butyl group, an isobutyl group, a n-pentyl group, a neopentyl group, a tert-pentyl group, a n-hexyl group, a n-octyl group, a n-decyl group, a n-dodecyl group, a n-pentadecyl group, an eicosyl group, a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (3,5-dimethylphenyl)methyl group, a (2,3,4-trimethylphenyl)methyl group, a (2,3,5-trimethylphenyl)methyl group, a (2,3,6-trimethylphenyl)methyl group, a (3,4,5-trimethylphenyl)methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, a (n-propylphenyl)methyl group, an (isopropylphenyl)methyl group, a (n-butylphenyl)methyl group, a (sec-butylphenyl)methyl group, a (tert-butylphenyl)methyl group, a (n-pentylphenyl)methyl group, a (neopentylphenyl)methyl group, a (n-hexylphenyl)methyl group, a (n-octylphenyl)methyl group, a (n-decylphenyl)methyl group, a (n-tetradecyphenyl)methyl group, a naphthylmethyl group, an anthracenylmethyl group, a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,4,6-trimethylphenyl group, a 2,3,5,6-tetramethylphenyl group, a pentamethylphenyl group, an ethylphenyl group, a n-propylphenyl group, an isopropylphenyl group, a n-butylphenyl group, a sec-butylphenyl group, a tert-butylphenyl group, a n-pentylphenyl group, a neopentylphenyl group, a n-hexylphenyl group, a n-octylphenyl group, a n-decylphenyl group, a n-dodecylphenyl group, a n-tetradecylphenyl group, a naphthyl group, and an anthracenyl group.

Examples of the oxygen atom-containing monovalent hydrocarbyl group of J in the formula (2) are a methoxy group, an ethoxy group, a n-propoxy group, an isopropoxy group, a n-butoxy group, a sec-butoxy group, a tert-butoxy group, a n-pentyloxy group, a neo-pentyloxy group, a n-hexyloxy group, a n-octyloxy group, a n-dodecyloxy group, a n-pentadecyloxy group, an eicosyloxy group, a phenoxy group, a 2-methylphenoxy group, a 3-methylphenoxy group, a 4-methylphenoxy group, a 2,3-dimethylphenoxy group, a 2,4-dimethylphenoxy group, a 2,5-dimethylphenoxy group, a 2,6-dimethylphenoxy group, a 3,4-dimethylphenoxy group, a 3,5-dimethylphenoxy group, a 2-tert-butyl-3-methylphenoxy group, a 2-tert-butyl-4-methylphenoxy group, a 2-tert-butyl-5-methylphenoxy group, a 2-tert-butyl-6-methylphenoxy group, a 2,3,4-trimethylphenoxy group, a 2,4,6-trimethylphenoxy group, a 2,6-di-tert-butyl-4-methylphenoxy group, a 2,3,5,6-tetramethylphenoxy group, a pentamethylphenoxy group, an ethylphenoxy group, a n-propylphenoxy group, an isopropylphenoxy group, a n-butylphenoxy group, a sec-butylphenoxy group, a tert-butylphenoxy group, a n-hexylphenoxy group, a n-octylphenoxy group, a n-decylphenoxy group, a n-tetradecylphenoxy group, a naphthoxy group, an anthracenoxy group, an acetoxy group, a propionyloxy group, a butyryloxy group, a neopentanoyloxy group, a 2-ethylhexanoyloxy group, a lauroyloxy group, a stearoyloxy group, a benzoyloxy group, a naphthoyloxy group, a 3-oxo-2-penten-2-oxy group, a 1-trifluoromethyl-3-oxo-1-buten-1-oxy group, a 1,3-bis(trifluoromethyl)-3-oxo-1-propen-1-oxy group, a 2,2,6,6-tetramethyl-5-oxo-4-hepten-2-oxy group, a 1-phenyl-3-oxo-1-buten-1-oxy group, a 2-methoxyphenyl group, a 3-methoxyphenyl group, a 4-methoxyphenyl group, a 2-ethoxyphenyl group, a 2-isopropoxyphenyl group, a 2-tert-butoxyphenyl group, a 2-phenoxyphenyl group, a 2-hydroxyphenyl group, a 2,3-dimethoxyphenyl group, a 2,4-dimethoxyphenyl group, a 2,6-dimethoxyphenyl group, a 2,4,6-trimethoxyphenyl group, a 2,3-diethoxyphenyl group, a 2,4-diethoxyphenyl group, a 2,6-diethoxyphenyl group, a 2,4,6-triethoxyphenyl group, a 2,3-diisopropoxyphenyl group, a 2,4-diisopropoxyphenyl group, a 2,6-diisopropoxyphenyl group, a 2,4,6-triisopropoxyphenyl group, a 2,3-di-tert-butoxyphenyl group, a 2,4-di-tert-butoxyphenyl group, a 2,6-di-tert-butoxyphenyl group, a 2,4,6-tri-tert-butoxyphenyl group, a 2,3-diphenoxyphenyl group, a 2,4-diphenoxyphenyl group, a 2,6-diphenoxyphenyl group, and a 2,4,6-triphenoxyphenyl group.

Examples of the two substituent-carrying monovalent amino group of J in the formula (2) are a dimethylamino group, a diethylamino group, a di-n-propylamino group, a diisopropylamino group, a di-n-butylamino group, a di-sec-butylamino group, a di-tert-butylamino group, a diisobutylamino group, a tert-butylisopropylamino group, a di-n-hexylamino group, a di-n-octylamino group, and a diphenylamino group.

J in the formula (2) is preferably a fluoro group, a chloro group, a bromo group, an iodo group, a methyl group, a butyl group, an allyl group, a methoxy group, an ethoxy group, an isopropoxy group, a tert-butoxy group, an acetoxy group, a propionyloxy group, a butyryloxy group, a neopentanoyloxy group, a 2-ethylhexanoyloxy group, a lauroyloxy group, a stearoyloxy group, a benzoyloxy group, a naphthoyloxy group, a 3-oxo-2-penten-2-oxy group, a 1-trifluoromethyl-3-oxo-1-buten-1-oxy group, a 1,3-bis(trifluoromethyl)-3-oxo-1-propen-1-oxy group, a 2,2,6,6-tetramethyl-5-oxo-4-hepten-2-oxy group, or a 1-phenyl-3-oxo-1-buten-1-oxy group, and more preferably is a fluoro group, a chloro group, an acetoxy group, a 2-ethylhexanoyloxy group, a naphthoyloxy group, a 3-oxo-2-penten-2-oxy group, a 1,3-bis(trifluoromethyl)-3-oxo-1-propen-1-oxy group, a 2,2,6,6-tetramethyl-5-oxo-4-hepten-2-oxy group, or a 1-phenyl-3-oxo-1-buten-1-oxy group.

The above definition of M in the formula (2), "group bound to the chromium atom with a lone electron-pair", means a neutral ligand bound to the chromium atom with a coordinate bond. Examples of said neutral ligand are an ether such as diethyl ether, tetrahydrofuran, dimethoxyethane, and dioxane; an alcohol such as methanol, ethanol, isopropanol, and 2-ethylhexanol; an ester such as ethyl acetate, isopropyl acetate, and butyl acetate; an amine such as triethylamine, N,N,N',N'-tetramethylethylenediamine, and 1,4,7-trimethyl-1,4,7-triazacyclononane; pyridine and its derivatives such as 4-methylpyridine, 4-ethylpyridine, 4-isopropylpyridine, 4-phenylpyridine, 2,6-dimethylpyridine, and quinoline; phosphine such as trimethylphosphine, triethylphosphine, tributylphosphine, triphenylphosphine, dimethylphenylphosphine, methyldiphenylphosphine, 1,2-bis(dimethylphosphino)ethane, 1,2-bis(diethylphosphino)ethane, 1,2-bis(diphenylphosphino)ethane, and 1,3-bis(diphenylphosphino)propane; phosphine oxide such as trimethylphosphine oxide, triethylphosphine oxide, and triphenylphosphine oxide; a nitrile such as acetonitrile and benzonitrile; an endo-on-form nitrogen molecule; and carbon monoxide. Among them, preferred is tetrahydrofuran, dioxane, isopropanol, 2-ethylhexanol, ethyl acetate, butyl acetate, 1,4,7-trimethyl-1,4,7-triazacyclononane, pyridine, 4-ethylpyridine, 4-isopropylpyridine, 4-phenylpyridine, tributylphosphine, triphenylphosphine, or triphenylphosphine oxide.

The above definition of M in the formula (2), "group bound to the chromium atom with π electrons", means a neutral ligand bound to the chromium atom with a multiple bond-orbital. Examples of said neutral ligand are an olefin such as ethylene and propylene; a diene such as butadiene, 2,4-hexadiene, and 1,4-diphenylbutadiene; a ketone such as acetone and benzophenone; and a side-on-form nitrogen molecule. Among them, preferred is an olefin or a diene, and more preferred is ethylene, butadiene, 2,4-hexadiene, or 1,4-diphenylbutadiene.

Examples of the compound represented by the formula (2) are dimethylchromium(II), trimethylchromium(III), tetramethylchromium(IV), tris(η-allyl)chromium(III), tetrakis(η-allyl)dichromium(II), terakis(trimethylsilylmethyl)chromium(IV), tetraethoxychromium(IV), tetraisopropoxychromium(IV), tetra-tert-butoxychromium(IV), bis(acetate)chromium(II), tris(acetate)chromium(III), bis(propionate)chromium(II), tris(propionate)chromium(III), tris(butyrate)chromium(III), bis(2-ethylhexanoate)chromium(II), tris(2-ethylhexanoate)chromium(III), tris(oxy-2-ethylhexanoate)chromium(III), tris(dichloroethylhexanoate)chromium(III), bis(neopentanoate)chromium(II), tris(neopentanoate)chromium(III), bis(laurate)chromium(II), tris(laurate)chromium(III), bis(stearate)chromium(II), tris(stearate)chromium(III), bis(benzoate)chromium(II), tris(benzoate)chromium(III), bis(naphthenoate)chromium(II), tris(naphthenoate)chromium(III), (oxalate)chromium(II), bis(acetylacetonate)chromium(II), tris(acetylacetonate)chromium(III), tris(trifluoroacetylacetonate)chromium(III), tris(hexafluoroacetylacetonate)chromium(III), (2,2,6,6-tetramethyl-3,5-heptanedionate)chromium(III), tris(benzoylacetonate)chromium(III), difluorochromium(II), trifluorochromium(III), dichlorochromium(II), trichlorochromium(III), dibromochromium(II), tribromochromium(III), diiodochromium(II), and triiodochromium(III).

Further examples of the compound represented by the formula (2) are trichlorotri(aniline)chromium(III), dichlorobis(pyridine)chromium(II), dichlorobis(4-ethylpyridine)chromium(II), trichlorotri(pyridine)chromium(III), trichlorotris(4-isopropylpyridine)chromium(III), trichlorotris(4-ethylpyridine)chromium(III), trichlorotris(4-phenylpyridine)chromium(III), trichloro(1,4,7-trimethyl-1,4,7-triazacyclononane)-chromium(III), dichlorobis(triphenylphosphine oxide)chromium(II), trichlorotris(triphenylphosphine)chromium(III), trichlorobis(tributylphosphine)chromium(III) dimer, trichlorotris(ethyl acetate)chromium(III), trichlorobis(butyl acetate)chromium(III), trichlorotris(tetrahydrofuran)chromium(III), trichlorotris(dioxane)chromium(III), trichlorotris(isopropanol)chromium(III), and trichlorotris(2-ethylhexanol)chromium(III); and compounds having the term "tribromo" or "triiodo" in place of the term "trichloro" contained in the above-exemplified compounds.

Among them, preferred is trimethylchromium(III), tris(2-ethylhexanoate)chromium(III), trichlorochromium(III), tribromochromium(III), trichlorotris(tetrahydrofuran)chromium(III), or tribromotris(tetrahydrofuran)chromium(III), from a viewpoint of higher productivity of an olefin oligomer.

A in the formula (1) regarding the step (2) is preferably a phosphorus atom from a viewpoint of higher productivity of an olefin oligomer.

Examples of G in the formula (1) are a methylene group, an ethylene group, an isopropylidene group, a 1,2-phenylene group, a 1,3-phenylene group, a 1,4-phenylene group, a dimethylsilylene group, a diethylsilylene group, a diphenylsilylene group, a dimethylgermylene group, a diphenylgermylene group, an —N($R^5$)— group, a —P($R^6$)— group, and a —B($R^7$)— group, wherein $R^5$, $R^6$, and $R^7$ are a hydrogen atom or a hydrocarbyl group. Among them, preferred is an —N($R^5$)— group, and $R^5$ is preferably a methyl group, an ethyl group, an isopropyl group, or a phenyl group.

Examples of the hydrocarbyl group of $R^1$, $R^2$, $R^3$ and $R^4$ in the formula (1) are those exemplified as J in the formula (2).

Examples of the halogenated hydrocarbyl group of $R^1$, $R^2$, $R^3$ and $R^4$ in the formula (1) are a fluoromethyl group, a difluoromethyl group, a trifluoromethyl group, a chloromethyl group, a dichloromethyl group, a trichloromethyl group, a bromomethyl group, a dibromomethyl group, a tribromomethyl group, an iodomethyl group, a diiodomethyl group, a triiodomethyl group, a fluoroethyl group, a difluoroethyl group, a trifluoroethyl group, a tetrafluoroethyl group, a pentafluoroethyl group, a chloroethyl group, a dichloroethyl group, a trichloroethyl group, a tetrachloroethyl group, a pentachloroethyl group, a bromoethyl group, a dibromoethyl group, a tribromoethyl group, a tetrabromoethyl group, a pentabromoethyl group, a perfluoropropyl group, a perfluorobutyl group, a perfluoropentyl group, a perfluorohexyl group, a perfluorooctyl group, a perfluorododecyl group, a perfluoropentadecyl group, a perfluoroeicosyl group, a perchloropropyl group, a perchlorobutyl group, a perchloropentyl group, a perchlorohexyl group, a perchlorooctyl group, a perchlorododecyl group, a perchloropentadecyl group, a perchloroeicosyl group, a perbromopropyl group, a perbromobutyl group, a perbromopentyl group, a perbromohexyl group, a perbromooctyl group, a perbromododecyl group, a perbromopentadecyl group, a perbromoeicosyl group, a 2-fluoropheny group, a 3-fluoropheny group, a 4-fluoropheny group, a 2-chloropheny group, a 3-chloropheny group, a 4-chloropheny group, a 2-bromopheny group, a 3-bromopheny group, a 4-bromopheny group, a 2-iodopheny group, a 3-iodopheny group, a 4-iodopheny group, a 2,4-difluoropheny group, a 2,6-difluoropheny group, a 2,4-dichloropheny group, a 2,6-dichloropheny group, a 2,4-dibromopheny group, a 2,6-dibromopheny group, a 2,4-diiodopheny group, a 2,6-diiodopheny group, a 2,4,6-trifluoropheny group, a 2,4,6-trichloropheny group, a 2,4,6-tribromopheny group, a 2,4,6-triiodopheny group, a 2,3,5,6-tetrafluoropheny group, a 2,3,5,6-tetrachloropheny group, a 2,3,5,6-tetrabromopheny group, a 2,3,5,6-tetraiodopheny group, a pentafluoropheny group, a pentachloropheny group, a pentabromopheny group, a pentaiodopheny group, a 2-trifluoromethylpheny group, a 3-trifluoromethylpheny group, a 4-trifluoromethylpheny group, a 2,4-bis(trifluoromethyl)pheny group, a 2,6-bis(trifluoromethyl)pheny group, and a 2,4,6-tris(trifluoromethyl)pheny group.

Examples of the oxygen-containing hydrocarbyl group of $R^1$, $R^2$, $R^3$ and $R^4$ in the formula (1) are those exemplified as J in the formula (2).

Examples of the sulfur-containing hydrocarbyl group of $R^1$, $R^2$, $R^3$ and $R^4$ in the formula (1) are a methylthio group, an ethylthio group, a n-propylthio group, an isopropylthio group, a n-butylthio group, a sec-butylthio group, a tert-butylthio group, a n-pentylthio group, a neopentylthio group, a n-hexylthio group, a n-octylthio group, a n-dodecylthio group, a n-pentadecylthio group, a n-eicosylthio group, a phenylthio group, a 2-methylphenylthio group, a 3-methylphenylthio group, a 4-methylphenylthio group, a 2,3-dimethylphenylthio group, a 2,4-dimethylphenylthio group, a 2,5-dimethylphenylthio group, a 2,6-dimethylphenylthio group, a 3,4-dimethylphenylthio group, a 3,5-dimethylphenylthio group, a 2-tert-butyl-3-methylphenylthio group, a 2-tert-butyl-4-methylphenylthio group, a 2-tert-butyl-5-methylphenylthio group, a 2-tert-butyl-6-methylphenylthio group, a 2,3,4-trimethylphenylthio group, a 2,4,6-trimethylphenylthio group, a 2,6-di-tert-butyl-4-methylphenylthio group, a 2,3,5,6-tetramethylphenylthio group, a pentamethylphenylthio group, an ethylphenylthio group, a n-propylphenylthio group, an isopropylphenylthio group, a n-butylphenylthio group, a sec-butylphenylthio group, a tert-butylphenylthio group, a n-hexylphenylthio group, a n-octylphenylthio group, a n-decylphenylthio group, a n-tetradecylphenylthio group, a naphthylthio group, an anthracenylthio group, a 2-methylthiophenyl group, a 3-methylthiophenyl group, a 4-methylthiophenyl group, a 2-ethylthiophenyl group, a 2-isopropylthiophenyl group, a 2-tert-butylthiophenyl group, a 2-phenylthiophenyl group, a 2-mercaptophenyl group, a 2,3-di(methylthio)phenyl group, a 2,4-di(methylthio)phenyl group, a 2,6-di(methylthio)phenyl group, a 2,4,6-tri(methylthio)phenyl group, a 2,3-di(ethylthio)phenyl group, a 2,4-di(ethylthio)phenyl group, a 2,6-di(ethylthio)phenyl group, a 2,4,6-tri(ethylthio)phenyl group, a 2,3-di(isopropylthio)phenyl group, a 2,4-di(isopropylthio)phenyl group, a 2,6-di(isopropylthio)phenyl group, a 2,4,6-tri(isopropylthio)phenyl group, a 2,3-di(tert-butylthio)phenyl group, a 2,4-di(tert-butylthio)phenyl group, a 2,6-di(tert-butylthio)phenyl group, a 2,4,6-tri(tert-butylthio)phenyl group, a 2,3-di(phenylthio)phenyl group, a 2,4-di(phenylthio)phenyl group, a 2,6-di(phenylthio)phenyl group, and a 2,4,6-tri(phenylthio)phenyl group.

Examples of the selenium-containing hydrocarbyl group of $R^1$, $R^2$, $R^3$ and $R^4$ in the formula (1) are a methylseleno group, an ethylseleno group, a n-propylseleno group, an isopropylseleno group, a n-butylseleno group, a sec-butylseleno group, a tert-butylseleno group, a n-pentylseleno group, a neopentylseleno group, a n-hexylseleno group, a n-octylseleno group, a n-dodecylseleno group, a n-pentadecylseleno group, a n-eicosylseleno group, a phenylseleno group, a 2-methylphenylseleno group, a 3-methylphenylseleno group, a 4-methylphenylseleno group, a 2,3-dimethylphenylseleno group, a 2,4-dimethylphenylseleno group, a 2,5-dimethylphenylseleno group, a 2,6-dimethylphenylseleno group, a 3,4-dimethylphenylseleno group, a 3,5-dimethylphenylseleno group, a 2-tert-butyl-3-methylphenylseleno group, a 2-tert-butyl-4-methylphenylseleno group, a 2-tert-butyl-5-methylphenylseleno group, a 2-tert-butyl-6-methylphenylseleno group, a 2,3,4-trimethylphenylseleno group, a 2,4,6-trimethylphenylseleno group, a 2,6-di-tert-butyl-4-methylphenylseleno group, a 2,3,5,6-tetramethylphenylseleno group, a pentamethylphenylseleno group, an ethylphenylseleno group, a n-propylphenylseleno group, an isopropylphenylseleno group, a n-butylphenylseleno group, a sec-butylphenylseleno group, a tert-butylphenylseleno group, a n-hexylphenylseleno group, a n-octylphenylseleno group, a n-decylphenylseleno group, a n-tetradecylphenylseleno group, a naphthylseleno group, an anthracenylseleno group, a 2-methylselenophenyl group, a 3-methylselenophenyl group, a 4-methylselenophenyl group, a 2-ethylselenophenyl group, a 2-isopropylselenophenyl group, a 2-tert-butylselenophenyl group, a 2-phenylselenophenyl group, a 2-selenophenyl group, a 2,3-di(methylseleno)phenyl group, a 2,4-di(methylseleno)phenyl group, a 2,6-di(methylseleno)phenyl group, a 2,4,6-tri(methylseleno)phenyl group, a 2,3-di(ethylseleno)phenyl group, a 2,4-di(ethylseleno)phenyl group, a 2,6-di(ethylseleno)phenyl group, a 2,4,6-tri(ethylseleno)phenyl group, a 2,3-di(isopropylseleno)phenyl group, a 2,4-di(isopropylseleno)phenyl group, a 2,6-di(isopropylseleno)phenyl group, a 2,4,6-tri(isopropylseleno)phenyl group, a 2,3-di(tert-butylseleno)phenyl group, a 2,4-di(tert-butylseleno)phenyl group, a 2,6-di(tert-butylseleno)phenyl group, a 2,4,6-tri(tert-butylseleno)phenyl group, 2,3-di(phenylseleno)phenyl group, a 2,4-di(phenylseleno)phenyl group, a 2,6-di(phenylseleno)phenyl group, and a 2,4,6-tri(phenylseleno)phenyl group.

Examples of the tellurium-containing hydrocarbyl group of $R^1$, $R^2$, $R^3$ and $R^4$ in the formula (1) are groups having the term "telluro" in place of the term "seleno" contained in the above-exemplified groups as the selenium-containing hydrocarbyl group.

Among them, $R^1$, $R^2$, $R^3$ and $R^4$ are preferably a phenyl group or a substituent-containing phenyl group, and more preferably a phenyl group, a 2-tolyl group, a 2-ethylphenyl group, a 2-isopropylphenyl group, a 2-phenylphenyl group, a 2-methoxyphenyl group, a 2-methylthiophenyl group, a 2-methylselenophenyl group, a 2-fluorophenyl group, a 3-methoxyphenyl group, a 4-methoxyphenyl group, a 2-ethoxyphenyl group, a 2-isopropoxyphenyl group, a 2-hydroxyphenyl group, a 2,3-dimethoxyphenyl group, a 2,4-dimethoxyphenyl group, a 2,6-dimethoxyphenyl group, or a 2,4,6-trimethoxyphenyl group.

Examples of the compound represented by the formula (1) are (phenyl)$_2$PN(methyl)P(phenyl)$_2$, (phenyl)$_2$PN(isopropyl)P(phenyl)$_2$, (2-tolyl)$_2$PN(methyl)P(2-tolyl)$_2$, (2-tolyl)$_2$PN(isopropyl)P(2-tolyl)$_2$, (2-ethylphenyl)$_2$PN(methyl)P(2-ethylphenyl)$_2$, (2-ethylphenyl)$_2$PN(isopropyl)P(2-ethylphenyl)$_2$, (2-isopropylphenyl)$_2$PN(methyl)P(2-isopropylphenyl)$_2$, (2-isopropylphenyl)$_2$PN(isopropyl)P(2-isopropylphenyl)$_2$, (2-ethylphenyl)(phenyl)PN(methyl)P(phenyl)$_2$, (2-methoxyphenyl)(phenyl)PN(methyl)P(phenyl)$_2$, (2-methoxyphenyl)(phenyl)PN(methyl)P(2-methoxyphenyl)(phenyl), (2-methoxyphenyl)$_2$PN(methyl)P(phenyl)$_2$, (2-methoxyphenyl)$_2$PN(methyl)P(2-methoxyphenyl)(phenyl), (2-ethylphenyl)(phenyl)PN(isopropyl)P(phenyl)$_2$, (2-methoxyphenyl)(phenyl)PN(isopropyl)P(phenyl)$_2$, (2-methoxyphenyl)(phenyl)PN(isopropyl)P(2-methoxyphenyl)(phenyl), (2-methoxyphenyl)$_2$PN(isopropyl)P(phenyl)2, (2-methoxyphenyl)$_2$PN(isopropyl)P(2-methoxyphenyl)(phenyl), (2-methoxyphenyl)$_2$PN(methyl)P(2-methoxyphenyl)$_2$, (2-methoxyphenyl)$_2$PN(ethyl)P(2-methoxyphenyl)2, (2-methoxyphenyl)$_2$PN(isopropyl)P(2-methoxyphenyl)2, (2-methoxyphenyl)$_2$PN(phenyl)P(2-methoxyphenyl)$_2$, (3-methoxyphenyl)$_2$PN(methyl)P(3-methoxyphenyl)$_2$, (4-methoxyphenyl)$_2$PN(methyl)P(4-methoxyphenyl)2, (2,3-dimethoxyphenyl)$_2$PN(methyl)P(2,3-dimethoxyphenyl)$_2$, (2,4-dimethoxyphenyl)$_2$PN(methyl)P(2,4-dimethoxyphenyl)$_2$, (2,6-dimethoxyphenyl)$_2$PN(methyl)P(2,6-dimethoxyphenyl)$_2$, and (2-fluorophenyl)$_2$PN(methyl)P(2-fluorophenyl)$_2$.

Among them, preferred is (phenyl)$_2$PN(isopropyl)P(phenyl)$_2$, (2-tolyl)$_2$PN(methyl)P(2-tolyl)$_2$, (2-ethylphenyl)$_2$PN(methyl)P(2-ethylphenyl)$_2$, (2-ethylphenyl)(phenyl)PN(methyl)P(phenyl)$_2$, (2-methoxyphenyl)(phenyl)PN(isopropyl)P(2-methoxyphenyl) (phenyl), (2-methoxyphenyl)$_2$PN(methyl)P(2-methoxyphenyl)$_2$, or (2-methoxyphenyl)$_2$PN(isopropyl)P(2-methoxyphenyl)$_2$, from a viewpoint of higher productivity of an olefin oligomer.

An example of a method for contacting the transition metal compound with the compound represented by the formula (1) in the step (2) is a method comprising the sub-steps of (2-1) feeding separately a solution containing the transition metal compound and a solution containing the compound represented by the formula (1) to a reactor, and (2-2) contacting them in the reactor. The step (2) is carried out usually at a temperature of −70 to 100° C. and usually under a pressure of atmospheric pressure to 0.1 MPa. The most suitable contact time in the step (2) depends upon a combination of the transition metal compound with the compound represented by the formula (1), and said contact time is preferably 1 minute to 24 hours. The contact time of shorter than 1 minute may result in insufficient productivity of an olefin oligomer.

The compound represented by the formula (1) is used in the step (2) in an amount of preferably 0.1 to 10 parts by mol per 1 part by mol of the transition metal compound. Said amount of larger than 10 parts by mol may result in insufficient productivity of an olefin oligomer, and said amount of smaller than 0.1 part by mol may result in low selectivity of an intended olefin oligomer.

When the above-exemplified contact method comprising the sub-steps (2-1) and (2-2) is used in the step (2), the solvent contained in the reaction mixture may be removed in order to obtain a solid and make a mixture of said solid with another solvent, said mixture being used in the step (3) as the contact product (ii).

The alumoxane compound in the present invention means a compound containing both a direct bond between a carbon atom and an aluminum atom and a direct bond between an oxygen atom and an aluminum atom. Examples of the alumoxane compound are those represented by the following formula (3) or (4):

  (3)

  (4).

In the formula (3), $E^2$ is a hydrocarbyl group, and plural $E^2$s are the same as, or different from one another; and b is an integer of 2 or larger, and preferably 2 to 40. An example of said hydrocarbyl group is an alkyl group such as a methyl group, an ethyl group, a n-propyl group, an isopropyl group, a n-butyl group, an isobutyl group, a n-pentyl group, and a neopentyl group. Among them, preferred is a methyl group or an isobutyl group.

In the formula (4), $E^3$ is a hydrocarbyl group, and plural $E^3$s are the same as, or different from one another; and c is an integer of 1 or larger, and preferably 1 to 40. An example of said hydrocarbyl group is an alkyl group such as a methyl group, an ethyl group, a n-propyl group, an isopropyl group, a n-butyl group, an isobutyl group, a n-pentyl group, and a neopentyl group. Among them, preferred is a methyl group or an isobutyl group.

A process for producing the compound represented by the formula (3) or (4) is not particularly limited. Examples of the process are (I) a process known in the art comprising the step of contacting water with a solution of a trialkylaluminum (for example, trimethylaluminum) in an organic solvent (for example, benzene and an aliphatic hydrocarbon), and (II) a process known in the art comprising the step of contacting a crystal water-containing metal salt (for example, hydrated copper sulfate) with a trialkylaluminum (for example, trimethylaluminum).

The step (3) is not limited in its method for contacting the contact product (i), the contact product (ii), the alumoxane compound, and optionally an olefin with one another. From a viewpoint of higher productivity of an olefin oligomer, preferred is (I) a method comprising the sub-steps of (3-1) contacting the contact product (ii) with the alumoxane compound (preferably, a solution containing the alumoxane compound), thereby producing a resultant contact product, and (3-2) contacting the resultant contact product, the contact product (i), and optionally an olefin with one another, or (II) a method comprising the sub-steps of (3-1) contacting the contact product (i) with the contact product (ii), thereby producing a resultant contact product, and (3-2) contacting the resultant contact product, the alumoxane compound (preferably, a solution containing the alumoxane compound), and optionally an olefin with one another.

The step (3) is carried out usually at a temperature of −70 to 200° C. and usually under a pressure of 0.01 to 10 MPa. A contact time in the step (3) is usually 1 minute to 24 hours, and preferably 30 minutes to 6 hours. The contact time of shorter than 1 minute may result in insufficient productivity of an olefin oligomer.

The olefin used in the step (1) forms the olefin oligomer in the present invention. However, when the optional olefin is used in the step (3), said olefin also forms the olefin oligomer, and therefore, more amount of the olefin oligomer can be produced in the present invention.

The olefin oligomer in the present invention means an addition product of a small number of olefin molecules. Examples of the addition product are a dimer of an olefin, a trimer thereof, and a tetramer thereof. Said addition product is an important comonomer for producing a polyolefin. Among them, a trimer of ethylene (1-hexene) and a tetramer thereof (1-octene) are particularly important from an industrial point of view.

EXAMPLE

The present invention is explained with reference to the following Examples, which do not limit the scope of the present invention.

Example 1

A glass vessel having a 50 mL inner-volume and equipped with a stirrer was dried in a vacuum, and then it was purged with a nitrogen gas. There were supplied thereto 5.0 mL of a tetrahydrofuran solution having a concentration of 2.0 mmol/L of trichlorotris(tetrahydrofuran)chromium(III) (transition metal compound represented by the formula (2)), and 5.0 mL of a tetrahydrofuran solution having a concentration of 2.0 mmol/L of (2-methoxyphenyl)$_2$PN(methyl)P (2-methoxyphenyl)$_2$ (compound represented by the formula (1)), and the resultant mixture was stirred for two hours at room temperature to obtain a reaction mixture. The solvent (tetrahydrofuran) contained in the reaction mixture was evaporated to dryness under reduced pressure, thereby obtaining a solid. Said solid was supplied with 10 mL of toluene to produce a suspension (a) containing a chromium atom in a concentration of 1.0 mmol/L.

An autoclave having a 0.4 L inner-volume and equipped with a stirrer was dried in a vacuum, and then it was purged with an argon gas. There was supplied thereto 80 mL of toluene as a solvent, and the autoclave was heated until said solvent reached a temperature of 80° C. An ethylene gas (olefin) was supplied thereto until a partial pressure thereof reached 2.0 MPa, and then 0.25 mL of a toluene solution having a concentration of 1.0 mol/L of tri-n-octylaluminum (organoaluminum compound) was supplied thereto, thereby producing a reaction mixture.

Said reaction mixture was supplied with 2.5 mL of the above-produced suspension (a), and 0.95 mL of a toluene solution having an aluminum atom-concentration of 3.15 mol-Al/L of methylalumoxane (alumoxane compound) and having a trade-name of PMAO-S manufactured by Tosoh-finechem, in this order, the former amount 2.5 mL containing 2.5 µmol of a chromium atom. The reaction was carried out at 80° C. for 60 minutes under an ethylene-partial pressure of 2.0 MPa. The autoclave was supplied with 2.5 mL of ethanol to stop the reaction.

The so-obtained reaction mixture was analyzed by a gas chromatography, and it was found that the reaction mixture contained 0.0% by weight of 1-butene, 87.1% by weight of 1-hexene, 0.8% by weight of 1-octene, 5.0% by weight of 1-decene, 0.1% by weight of 1-dodecene, and 0.2% by weight of 1-tetradecene, the total amount of the reaction mixture excluding toluene (solvent) being 100% by weight.

The yield of 1-hexene was 45.2 kg per one mmol of a chromium atom, which was calculated from (i) the above-mentioned content of 1-hexene (87.1% by weight), (ii) the above-mentioned total amount of the reaction mixture excluding toluene (solvent), and (iii) the above-mentioned amount of the chromium atom (2.5 µmol).

Also, the reaction mixture was poured into a hydrochloric acid-ethanol mixed liquid having a hydrogen chloride-concentration of 0.05% by weight, and the resultant precipitated solid was washed with ethanol. The washed solid was air-dried at room temperature, and then further dried under a reduced pressure, thereby obtaining 2.2 g of the solid, which corresponded to 1.7% by weight, the total amount of the reaction mixture excluding toluene (solvent) being 100% by weight. Said solid was considered to be largely an ethylene polymer.

The above-mentioned analysis by a gas chromatography was carried out under the following conditions, which can determine quantity of products having 4 to 20 carbon atoms:

equipment of Type GC-2010 manufactured by Shimadzu Corporation;

column of Type DB-1 having 60 m-total length, 0.25 mm inner-diameter, and 0.25 µm-film thickness, manufactured by J & W Scientific, wherein the film thickness means thickness of a silanol-made film coated on a material ($SiO_2$) packed into the column to separate the products having 4 to 20 carbon atoms from one another;

carrier gas of helium;

injection temperature of 230° C.;

detector temperature of 230° C.;

internal standard material of cyclohexane; and injected amount of 2 µL of a sample (reaction mixture).

The column temperature was controlled as follows:

(1) injecting a sample at column temperature of 40° C.;

(2) retaining 40° C. for 16 minutes;

(3) raising column temperature from 40° C. to 230° C. at a rate of 8° C./minute; and (4) retaining 230° C. for 5 minutes, all olefin oligomers contained in the sample being ejected from the column within said retention time.

Example 2

Example 1 was repeated except that the amount of the toluene solution having a concentration of 1.0 mol/L of tri-n-octylaluminum (organoaluminum compound) was changed from 0.25 mL to 0.50 mL, thereby obtaining a reaction mixture.

The so-obtained reaction mixture was analyzed similarly by a gas chromatography, and it was found that the reaction mixture contained 0.0% by weight of 1-butene, 87.5% by weight of 1-hexene, 0.8% by weight of 1-octene, 5.4% by weight of 1-decene, 0.1% by weight of 1-dodecene, and 0.2% by weight of 1-tetradecene, the total amount of the reaction mixture excluding toluene (solvent) being 100% by weight. The yield of 1-hexene was calculated to be 43.2 kg per one mmol of a chromium atom.

Similarly to the above, the reaction mixture was poured into a hydrochloric acid-ethanol mixed liquid, and the resultant precipitated solid was washed with ethanol. The washed solid was air-dried at room temperature, and then further dried under a reduced pressure, thereby obtaining 0.4 g of the solid, which corresponded to 0.3% by weight, the total amount of the reaction mixture excluding toluene (solvent) being 100% by weight. Said solid was considered to be largely an ethylene polymer.

Example 3

A glass vessel having a 50 mL inner-volume and equipped with a stirrer was dried in a vacuum, and then it was purged with a nitrogen gas. There were supplied thereto 5.0 mL of a tetrahydrofuran solution having a concentration of 2.0 mmol/L of trichlorotris(tetrahydrofuran)chromium(III) (transition metal compound represented by the formula (2)), and 5.0 mL of a tetrahydrofuran solution having a concentration of 2.0 mmol/L of (2-methoxyphenyl)$_2$PN(methyl)P(2-methoxyphenyl)$_2$ (compound represented by the formula (1)), and the resultant mixture was stirred for two hours at room temperature to obtain a reaction mixture. The solvent (tetrahydrofuran) contained in the reaction mixture was evaporated to dryness under reduced pressure, thereby obtaining a solid.

Said solid was supplied with 9.05 mL of toluene, and 0.95 mL of a toluene solution having an aluminum atom-concentration of 3.15 mol-Al/L of methylalumoxane (alumoxane compound) and having a trade-name of PMAO-S manufactured by Tosoh-finechem, in this order, thereby producing a suspension (b) containing a chromium atom in a concentration of 1.0 mmol/L, and an aluminum atom in a concentration of 0.3 mol/L.

An autoclave having a 0.4 L inner-volume and equipped with a stirrer was dried in a vacuum, and then it was purged with an argon gas. There was supplied thereto 80 mL of toluene as a solvent, and the autoclave was heated until said solvent reached a temperature of 80° C. An ethylene gas (olefin) was supplied thereto until a partial pressure thereof reached 2.0 MPa, and then, 0.30 mL of a toluene solution having a concentration of 1.0 mol/L of trimethylaluminum (organoaluminum compound), and 2.5 mL (containing 2.5 µmol of a chromium atom) of the above-produced suspension (b) were supplied thereto in this order, thereby starting the reaction. The reaction was carried out at 80° C. for 60 minutes under an ethylene-partial pressure of 2.0 MPa. The autoclave was supplied with 2.5 mL of ethanol to stop the reaction.

The so-obtained reaction mixture was analyzed by a gas chromatography, and it was found that the reaction mixture contained 0.0% by weight of 1-butene, 85.0% by weight of 1-hexene, 0.9% by weight of 1-octene, 5.2% by weight of 1-decene, 0.1% by weight of 1-dodecene, and 0.2% by weight of 1-tetradecene, the total amount of the reaction mixture excluding toluene (solvent) being 100% by weight. The yield of 1-hexene was calculated to be 44.5 kg per one mmol of a chromium atom.

Similarly to the above, the reaction mixture was poured into a hydrochloric acid-ethanol mixed liquid, and the resultant precipitated solid was washed with ethanol. The washed solid was air-dried at room temperature, and then further dried under a reduced pressure, thereby obtaining 4.1 g of the solid, which corresponded to 3.1% by weight, the total amount of the reaction mixture excluding toluene (solvent) being 100% by weight. Said solid was considered to be largely an ethylene polymer.

Example 4

A glass vessel having a 50 mL inner-volume and equipped with a stirrer was dried in a vacuum, and then it was purged with a nitrogen gas. There were supplied thereto 5.0 mL of a tetrahydrofuran solution having a concentration of 2.0 mmol/L of trichlorotris(tetrahydrofuran)chromium(III) (transition metal compound represented by the formula (2)), and 5.0 mL of a tetrahydrofuran solution having a concentration of 2.0 mmol/L of (2-methoxyphenyl)$_2$PN(methyl)P (2-methoxyphenyl)2 (compound represented by the formula (1)), and the resultant mixture was stirred for two hours at room temperature to obtain a reaction mixture. The solvent (tetrahydrofuran) contained in the reaction mixture was evaporated to dryness under reduced pressure, thereby obtaining a solid.

Said solid was supplied with 9.37 mL of toluene, and 0.63 mL of a toluene solution having an aluminum atom-concentration of 3.15 mol-Al/L of methylalumoxane (alumoxane compound) and having a trade-name of PMAO-S manufactured by Tosoh-finechem, in this order, thereby producing a suspension (c) containing a chromium atom in a concentration of 1.0 mmol/L, and an aluminum atom in a concentration of 0.2 mol/L.

An autoclave having a 0.4 L inner-volume and equipped with a stirrer was dried in a vacuum, and then it was purged with an argon gas. There was supplied thereto 80 mL of toluene as a solvent, and the autoclave was heated until said solvent reached a temperature of 80° C. An ethylene gas (olefin) was supplied thereto until a partial pressure thereof reached 2.0 MPa, and then, 0.080 mL of a toluene solution having an aluminum atom-concentration of 3.15 mol-Al/L of methylalumoxane (organoaluminum compound) and having a trade-name of PMAO-S manufactured by Tosoh-finechem, and 2.5 mL (containing 2.5 µmol of a chromium atom) of the above-produced suspension (c) were supplied thereto in this order, thereby starting the reaction. The reaction was carried out at 80° C. for 60 minutes under an ethylene-partial pressure of 2.0 MPa. The autoclave was supplied with 2.5 mL of ethanol to stop the reaction.

The so-obtained reaction mixture was analyzed by a gas chromatography, and it was found that the reaction mixture contained 0.0% by weight of 1-butene, 85.4% by weight of 1-hexene, 0.7% by weight of 1-octene, 6.4% by weight of 1-decene, 0.1% by weight of 1-dodecene, and 0.3% by weight of 1-tetradecene, the total amount of the reaction mixture excluding toluene (solvent) being 100% by weight. The yield of 1-hexene was calculated to be 45.6 kg per one mmol of a chromium atom.

Similarly to the above, the reaction mixture was poured into a hydrochloric acid-ethanol mixed liquid, and the resultant precipitated solid was washed with ethanol. The washed solid was air-dried at room temperature, and then further dried under a reduced pressure, thereby obtaining 0.03 g of the solid, which corresponded to 0.02% by weight, the total amount of the reaction mixture excluding toluene (solvent) being 100% by weight. Said solid was considered to be largely an ethylene polymer.

Comparative Example 1

Example 3 was repeated except that trimethylaluminum (organoaluminum compound) was not used, thereby obtaining a reaction mixture.

The so-obtained reaction mixture was analyzed by a gas chromatography, and it was found that the reaction mixture contained 0.0% by weight of 1-butene, 90.4% by weight of 1-hexene, 0.9% by weight of 1-octene, 5.5% by weight of 1-decene, 0.1% by weight of 1-dodecene, and 0.0% by weight of 1-tetradecene, the total amount of the reaction mixture excluding toluene (solvent) being 100% by weight. The yield of 1-hexene was calculated to be 37.9 kg per one mmol of a chromium atom, which was smaller than that (44.5 kg per one mmol thereof) in Example 3.

Similarly to the above, the reaction mixture was poured into a hydrochloric acid-ethanol mixed liquid, and the resultant precipitated solid was washed with ethanol. The washed solid was air-dried at room temperature, and then further dried under a reduced pressure, thereby obtaining 0.1 g of the solid, which corresponded to 0.1% by weight, the total amount of the reaction mixture excluding toluene (solvent) being 100% by weight. Said solid was considered to be largely an ethylene polymer.

Example 5

An autoclave having a 1 L inner-volume and equipped with a stirrer was dried in a vacuum, and then it was purged with an argon gas. There was supplied thereto 500 mL of toluene as a solvent, and the autoclave was heated until said solvent reached a temperature of 80° C. An ethylene gas (olefin) was supplied thereto until a partial pressure thereof reached 2.0 MPa, and then 0.080 mL of a toluene solution having an aluminum atom-concentration of 3.15 mol-Al/L of methylalumoxane (organoaluminum compound) and having a trade-name of PMAO-S manufactured by Tosoh-finechem was supplied thereto, thereby producing a reaction mixture.

Said reaction mixture was supplied with 2.5 mL (containing 2.5 µmol of a chromium atom) of the above-produced suspension (c) (see Example 4), thereby starting the reaction. The reaction was carried out at 80° C. for 60 minutes under an ethylene-partial pressure of 2.0 MPa. The autoclave was supplied with 2.5 mL of ethanol to stop the reaction.

The so-obtained reaction mixture was analyzed by a gas chromatography, and it was found that the reaction mixture contained 0.0% by weight of 1-butene, 91.8% by weight of 1-hexene, 1.4% by weight of 1-octene, 3.2% by weight of 1-decene, 0.1% by weight of 1-dodecene, and 0.1% by weight of 1-tetradecene, the total amount of the reaction mixture excluding toluene (solvent) being 100% by weight. The yield of 1-hexene was calculated to be 79.8 kg per one mmol of a chromium atom.

Similarly to the above, the reaction mixture was poured into a hydrochloric acid-ethanol mixed liquid, and the resultant precipitated solid was washed with ethanol. The washed solid was air-dried at room temperature, and then further dried under a reduced pressure, thereby obtaining 0.08 g of the solid, which corresponded to 0.04% by weight, the total amount of the reaction mixture excluding toluene (solvent) being 100% by weight. Said solid was considered to be largely an ethylene polymer.

Example 6

An autoclave having a 0.4 L inner-volume and equipped with a stirrer was dried in a vacuum, and then it was purged with an argon gas. There was supplied thereto 80 mL of toluene as a solvent, and the autoclave was heated until said solvent reached a temperature of 45° C. An ethylene gas (olefin) was supplied thereto until a partial pressure thereof reached 2.0 MPa, and then 0.25 mL of a toluene solution having a concentration of 1.0 mol/L of tri-n-octylaluminum (organoaluminum compound) was supplied thereto, thereby producing a reaction mixture.

There were mixed for 5 minutes, in a catalyst-feeder equipped to said autoclave, 1.5 mL of a toluene solution having a concentration of 10.0 mmol/L of chromium(III) tris(2-ethylhexanoate) (transition metal compound represented by the formula (2)), and 3.0 mL of a toluene solution having a concentration of 6.0 mmol/L of (phenyl)$_2$PN(isopropyl)P(phenyl)$_2$ (compound represented by the formula (1)), and the resultant mixture was supplied to the above-mentioned reaction mixture existing in said autoclave. Said autoclave was further supplied with 0.48 mL of a toluene solution having an aluminum atom-concentration of 3.15 mol-Al/L of methylalumoxane (alumoxane compound) and having a trade-name of PMAO-S manufactured by Tosoh-finechem, thereby starting the reaction. The reaction was carried out at 45° C. for 60 minutes under an ethylene-partial pressure of 2.0 MPa. The autoclave was supplied with 2.5 mL of ethanol to stop the reaction.

The so-obtained reaction mixture was analyzed by a gas chromatography, and it was found that the reaction mixture contained 0.7% by weight of 1-butene, 13.5% by weight of 1-hexene, 38.1% by weight of 1-octene, 0.7% by weight of 1-decene, 0.5% by weight of 1-dodecene, and 0.5% by weight of 1-tetradecene, the total amount of the reaction mixture excluding toluene (solvent) being 100% by weight. The yield of 1-octene was calculated to be 795 kg per one mmol of a chromium atom.

Similarly to the above, the reaction mixture was poured into a hydrochloric acid-ethanol mixed liquid, and the resultant precipitated solid was washed with ethanol. The washed solid was air-dried at room temperature, and then further dried under a reduced pressure, thereby obtaining 2.0 g of the solid, which corresponded to 37.4% by weight, the total amount of the reaction mixture excluding toluene (solvent) being 100% by weight. Said solid was considered to be largely an ethylene polymer.

Comparative Example 2

Example 6 was repeated except that tri-n-octylaluminum (organoaluminum compound) was not used, thereby obtaining a reaction mixture.

The so-obtained reaction mixture was analyzed by a gas chromatography, and it was found that the reaction mixture contained 0.5% by weight of 1-butene, 12.9% by weight of 1-hexene, 39.5% by weight of 1-octene, 0.7% by weight of 1-decene, 0.5% by weight of 1-dodecene, and 0.5% by weight of 1-tetradecene, the total amount of the reaction mixture excluding toluene (solvent) being 100% by weight. The yield of 1-octene was calculated to be 640 kg per one mmol of a chromium atom, which was smaller than that (795 kg per one mmol thereof) in Example 6.

Similarly to the above, the reaction mixture was poured into a hydrochloric acid-ethanol mixed liquid, and the resultant precipitated solid was washed with ethanol. The washed solid was air-dried at room temperature, and then further dried under a reduced pressure, thereby obtaining 1.5 g of the solid, which corresponded to 36.5% by weight, the total amount of the reaction mixture excluding toluene (solvent) being 100% by weight. Said solid was considered to be largely an ethylene polymer.

The invention claimed is:

1. A process for producing an olefin oligomer, which comprises the steps of:
   (1) contacting an olefin with an organoaluminum compound, thereby producing a contact product (i);
   (2) contacting a transition metal compound with a compound represented by the following formula (1), thereby producing a contact product (ii); and
   (3) contacting the contact product (i), the contact product (ii), an alumoxane compound, and optionally an olefin with one another;

$$R^1R^2A\text{-}G\text{-}AR^3R^4 \qquad (1)$$

wherein A is a nitrogen atom, a phosphorus atom, an arsenic atom or an antimony atom, and As are the same as or different from each other; G is a divalent group; and $R^1$, $R^2$, $R^3$ and $R^4$ are independently of one another a hydrocarbyl group, a halogenated hydrocarbyl group, an oxygen-containing hydrocarbyl group, a sulfur-containing hydrocarbyl group, a selenium-containing hydrocarbyl group, or a tellurium-containing hydrocarbyl group.

2. The process for producing an olefin oligomer according to claim 1, wherein the transition metal compound is a chromium compound, a molybdenum compound, or a tungsten compound.

3. The process for producing an olefin oligomer according to claim 1, wherein A in the formula (1) is a phosphorus atom.

4. The process for producing an olefin oligomer according to claim 1, wherein G in the formula (1) is an —N($R^5$)— group, $R^5$ being a hydrogen atom or a hydrocarbyl group.

5. The process for producing an olefin oligomer according to claim 1, wherein $R^1$, $R^2$, $R^3$ and $R^4$ in the formula (1) are independently of one another a phenyl group or a substituent-containing phenyl group.

6. The process for producing an olefin oligomer according to claim 1, wherein $R^1$, $R^2$, $R^3$ and $R^4$ in the formula (1) are independently of one another a phenyl group, a 2-tolyl group, a 2-ethylphenyl group, a 2-isopropylphenyl group, a 2-phenylphenyl group, a 2-methoxyphenyl group, a 2-methylthiophenyl group, a 2-methylselenophenyl group, a 2-fluorophenyl group, a 3-methoxyphenyl group, a 4-methoxyphenyl group, a 2-ethoxyphenyl group, a 2-isopropoxyphenyl group, a 2-hydroxyphenyl group, a 2,3-dimethoxyphenyl group, a 2,4-dimethoxyphenyl group, a 2,6-dimethoxyphenyl group, or a 2,4,6-trimethoxyphenyl group.

7. The process for producing an olefin oligomer according to claim 1, wherein the compound represented by the formula (1) is (phenyl)$_2$PN(isopropyl)P(phenyl)$_2$, (2-tolyl)$_2$PN(methyl)P(2-tolyl)$_2$, (2-ethylphenyl)$_2$PN(methyl)P(2-ethylphenyl)$_2$, (2-ethylphenyl)(phenyl)PN(methyl)P(phenyl)$_2$, (2-methoxyphenyl)(phenyl)PN(isopropyl)P(2-methoxyphenyl) (phenyl), (2-methoxyphenyl)$_2$PN(methyl)P(2-methoxyphenyl)$_2$, or (2-methoxyphenyl)$_2$PN(isopropyl)P(2-methoxyphenyl)$_2$.

8. The process for producing an olefin oligomer according to claim 1, wherein the step (3) comprises the sub-steps of (3-1) contacting the contact product (ii) with the alumoxane compound, thereby producing a resultant contact product, and (3-2) contacting the resultant contact product, the contact product (i), and optionally an olefin with one another.

9. The process for producing an olefin oligomer according to claim 1, wherein the step (3) comprises the sub-steps of (3-1) contacting the contact product (i) with the contact product (ii), thereby producing a resultant contact product, and (3-2) contacting the resultant contact product, the alumoxane compound, and optionally an olefin with one another.

10. The process for producing an olefin oligomer according to claim 1, wherein the olefin is ethylene, and the olefin oligomer is a trimer of ethylene, which is 1-hexene, or a tetramer of ethylene, which is 1-octene.

* * * * *